United States Patent
Ferguson

(10) Patent No.: US 6,905,594 B2
(45) Date of Patent: Jun. 14, 2005

(54) FILTER APPARATUS AND METHODS TO CAPTURE A DESIRED AMOUNT OF MATERIAL FROM A SAMPLE SUSPENSION FOR MONOLAYER DEPOSITION, ANALYSIS OR OTHER USES

(75) Inventor: Gary William Ferguson, Burnaby (CA)

(73) Assignee: G6 Science Corp. (CA)

( * ) Notice: Subject to any disclaimer, the term of this patent is extended or adjusted under 35 U.S.C. 154(b) by 0 days.

(21) Appl. No.: 10/269,220

(22) Filed: Oct. 11, 2002

(65) Prior Publication Data

US 2004/0069714 A1 Apr. 15, 2004

(51) Int. Cl.$^7$ ................................................ B01L 11/00
(52) U.S. Cl. ...................... 210/90; 210/100; 210/120; 73/863.02; 73/863.23; 422/101
(58) Field of Search ................................ 210/100, 120, 210/472, 416.1, 90, 97, 108; 55/311; 96/403; 137/461; 436/177, 178; 422/101; 435/286.1, 286.5, 286.6; 73/61.72, 61.73, 863.23, 863.02, 863.03

(56) References Cited

U.S. PATENT DOCUMENTS

| | | | |
|---|---|---|---|
| 1,726,839 A | * 9/1929 | Kasztory | ...................... 210/266 |
| 2,184,761 A | * 12/1939 | Wier | ........................... 210/100 |
| 2,323,021 A | * 6/1943 | Ernst | ........................... 137/475 |
| 2,632,566 A | * 3/1953 | Morrison | ...................... 210/100 |
| 3,591,003 A | 7/1971 | Cooper | |
| 3,630,360 A | * 12/1971 | Davis et al. | ................ 210/798 |
| 3,963,048 A | 6/1976 | Bowman | |
| 4,246,788 A | * 1/1981 | Olin et al. | ................ 73/863.03 |
| 4,250,830 A | 2/1981 | Leif | |
| 4,284,505 A | 8/1981 | Pope, Jr. et al. | |
| 4,319,996 A | 3/1982 | Vincent et al. | |
| 4,395,493 A | 7/1983 | Zahniser et al. | |
| 4,435,507 A | 3/1984 | Stenkvist | |
| 4,574,836 A | * 3/1986 | Barnard, Jr. | ................ 137/553 |

(Continued)

FOREIGN PATENT DOCUMENTS

| | | |
|---|---|---|
| EP | 1 094 311 A2 | 4/2001 |
| WO | WO 01/83089 | 11/2001 |

OTHER PUBLICATIONS

International Search Report dated Sep. 24, 2004 which Issued in connection with corresponding PCT application No. PCT/CA 03/01559.

*Primary Examiner*—Terry K. Cecil
(74) *Attorney, Agent, or Firm*—Trexler, Bushnell, Giangiorgi, Blackstone & Marr, Ltd.

(57) ABSTRACT

The present invention is a filter apparatus with methods to capture a desired amount of material suspended in a liquid or gas for monolayer deposition, analysis or other uses. Novel filter devices are employed to capture material which may be used for the purification or enrichment of various sample constituents or captured material may be observed or analyzed. Alternatively, particulate material may be used as a transport mechanism for proteins or chemicals which in turn may be assessed or used. The filter device employs sensors to sense pressure and adjust, halt or otherwise control sample flow. The pressure sensor essentially monitors the flow rate of sample suspension through a filter, typically responding at a predetermined pressure associated with capture of a desired amount of material on the filter. A separate valve or valve integrated with pressure sensing provides a means to adjust sample flow. Typically, pressure is used to cause the sample suspension to flow through the filter, which is preferably a membrane filter for monolayer deposition. In some embodiments a novel syringe provides this pressure, functioning as a vacuum source. The filter apparatus may be further automated to process a plurality of samples, simultaneously.

7 Claims, 4 Drawing Sheets

U.S. PATENT DOCUMENTS

| | | |
|---|---|---|
| 4,614,109 A | 9/1986 | Hofmann |
| 4,765,963 A | 8/1988 | Mukogawa et al. |
| 4,792,398 A | 12/1988 | Klein |
| 4,832,840 A | 5/1989 | Klinkau et al. |
| 4,961,432 A | 10/1990 | Guirguis |
| 4,967,791 A | 11/1990 | Sternberger |
| 4,969,997 A | 11/1990 | Kluver et al. |
| 4,996,627 A | 2/1991 | Zias et al. |
| 5,141,639 A | 8/1992 | Kraus et al. |
| 5,168,965 A | 12/1992 | Huang |
| D343,682 S | 1/1994 | Cattaoris |
| 5,312,380 A | 5/1994 | Alchas et al. |
| 5,341,838 A | 8/1994 | Powell |
| 5,358,690 A | 10/1994 | Guirguis |
| 5,422,273 A | 6/1995 | Garrison et al. |
| 5,429,803 A | 7/1995 | Guirguis |
| 5,471,994 A | 12/1995 | Guirguis |
| 5,480,484 A | 1/1996 | Kelley et al. |
| 5,500,167 A | 3/1996 | Degen |
| 5,561,556 A | 10/1996 | Weissman |
| 5,593,529 A | 1/1997 | Grimes |
| 5,603,827 A | 2/1997 | Hermann et al. |
| 5,679,154 A | 10/1997 | Kelley et al. |
| 5,744,034 A * | 4/1998 | Clapham et al. ............ 210/411 |
| 5,784,193 A | 7/1998 | Ferguson |
| 5,792,425 A | 8/1998 | Clark et al. |
| 5,849,505 A | 12/1998 | Guirguis |
| 5,976,824 A | 11/1999 | Gordon |
| 6,010,909 A | 1/2000 | Lapidus |
| 6,091,483 A | 7/2000 | Guirguis |
| 6,106,483 A | 8/2000 | Guirguis |
| 6,149,871 A | 11/2000 | Guirguis et al. |
| 6,162,401 A | 12/2000 | Callaghan |
| 6,210,909 B1 | 4/2001 | Guirguis |
| 6,215,892 B1 | 4/2001 | Douglass et al. |
| 6,225,125 B1 | 5/2001 | Lapidus |
| 6,286,372 B1 | 9/2001 | Von Rauch |
| 6,295,877 B1 | 10/2001 | Aboul-Hosn et al. |
| 6,296,764 B1 | 10/2001 | Guirguis |
| 6,309,362 B1 | 10/2001 | Guirguis et al. |
| 6,318,190 B1 | 11/2001 | Radcliffe et al. |
| 6,404,906 B2 | 6/2002 | Bacus et al. |
| 6,425,883 B1 | 7/2002 | Urich et al. |
| 6,579,447 B2 * | 6/2003 | Romanyszyn et al. ...... 210/108 |

* cited by examiner

FILTER APPARATUS AND METHODS TO CAPTURE A DESIRED AMOUNT OF MATERIAL FROM A SAMPLE SUSPENSION FOR MONOLAYER DEPOSITION, ANALYSIS OR OTHER USES

BACKGROUND OF INVENTION

In industry and biology it is often advantageous to capture particulate material from a sample suspension on a filter for purification, enrichment, observation or subsequent analysis. Once a desired amount of material is captured on a filter, it is sometimes advantageous to deposit an approximate monolayer of this material on a receiving surface for analysis, for example, biological cells may be captured on a membrane filter for deposition on a microscope slide for microscopic analysis.

As used herein, "sample suspension" means particulate material suspended in a liquid or gas. "Material" as used herein means biological cells, organisms, bacteria, viruses, or components of these, as well as organic and inorganic particulates or any other matter which may be captured or isolated on a filter. This captured material may provide diagnostic and/or analytical information or be re-suspended or otherwise used. For example, captured material may be analyzed chemically or may be placed on a receiving surface, such as a microscope slide for analysis.

The term "microscopic analysis" as used herein means a process wherein a microscope under human and/or machine control is used for visualization, analysis, and/or enumeration, and/or categorization, and/or photography, and/or electronic image acquisition of biological or other material. "Receiving surface" as used herein, means all discrete objects which serve as substrates to support material, for example a microscope slide, cover-glass, plastic sheet, semiconductor chip, strip of tape, etc.

The quantity and characteristics of particulate materials are important in manufacturing, for example, processes that utilize powders, pigments, fuels or lubricants. Particle evaluations are also used to assess contaminants in water or air such as pollen, asbestos and soot. Particulate material is sometimes used indirectly to assess proteins or chemicals, where it acts as a support medium, for example, beads coated with monoclonal antibody may be interacted with blood. Then these reacted beads may be captured on a filter and assessed for bound proteins or chemicals.

For a subset of applications that utilize filter capture, it is advantageous to work with a known or desired amount of material. Certain chemical methods, for example, rely on tightly controlled amounts of materials. Similarly, the concentration of material deposited on a receiving surface for microscopic analysis influences observation and analysis. When an excessive amount of material is deposited, microscopic analysis may be complicated, for example, when folding or overlapping material obscures adjacent material. Conversely, a well-formed monolayer of sparse material may also impede effective microscopic analysis by: extending the time required to locate material, reducing the ability to compare material within a field of view, diluting the diagnostic content or otherwise undermining effective analysis. "Monolayer" as used herein means a substantially two-dimensional, relatively uniformly distributed layer of material deposited on a receiving surface. For cytological applications, this material is predominately comprised of single cells and cell clusters. For some biological applications addition efforts are made to minimize the number of cells clusters. To accomplish this task, physical agitation and/or a disaggregating agent may be used to help disperse cells from tissue sections, clumps, or otherwise break-up and dissolve mucus components which are relatively common in cytological scrapings or lung sputum samples. Other applications, such as detecting malignancy-associated changes that rely on assessing DNA and DNA distribution, primarily in cell nuclei, benefit when a desired amount of material is present.

For some applications, controlling the amount of material deposited begins with assessing and adjusting the concentration of material in the sample suspension. Particle counters based on electrical impedance, light scatter, turbidity or other principles are often used to measure the concentration of material in suspension. Centrifugation, cell sorters, magnetic-beads, columns, density gradients, dilutions or other means may be used alone or in combination with these measurement methods to increase, decrease or otherwise adjust the concentration of material in a sample suspension. Once the sample concentration is known, or adjusted to a desired level, a controlled volume or set collection time could be used to gauge the amount of material captured on a filter.

Additionally, apparatus and methods are available to capture a material on a filter for monolayer deposition, however, controlling the amount of material collected on a filter is more difficult to achieve. Apparatus which provides for capturing a desired amount of material on a filter tend to be: relatively complex, expensive, require electronic control, are difficult to automate or are otherwise limited.

Therefore, a simple, reliable method of capturing a desired amount of material on a filter for monolayer deposition or other uses would be advantageous. The present invention is a filter device that provides a means to capture a desired amount of material from a sample suspension. To accomplish this, a pressure sensor is used substantially to monitor the flow rate of sample suspension through the filter and a separate or integrated valve further provides a means to control the sample flow rate and thus the collection of material. Once a desired amount of material is captured on a filter, such as a membrane with uniform, distributed pores, it may be transferred by contact to a receiving surface for observation or analysis.

BRIEF DISCUSSION OF PRIOR ART

U.S. Pat. No. 4,435,507 to Stenkvist, entitled "Process and device for preparation of cell samples for cytological tests" discloses a cell preparation device to generate a relatively homogenous cell suspension (slurry of free cells) from scrapings and other samples. This prior art also discusses some of the goals of sample preparation, along with typical solutions employed, such as fixatives or dispersing agents.

U.S. Pat. No. 6,296,764 to Guirguis, entitled "Apparatus for mixing and separating particulate matter from a fluid" discusses a rotatable agitator and issues related to efficiently collecting and concentrating particulate matter in a form readily accessible for microscopic examination. Also noted: "Conventional cell preparation techniques fail to adequately address the issues of non-uniform cell densities, uneven cell distribution and air drying artifacts."

U.S. Pat. Nos. 5,471,994, 6,091,483 and 6,106,483 also to Guirguis show material capture on various membranes. And in U.S. Pat. No. 4,961,432, entitled "Modular fluid sample preparation assembly", Guirguis discusses a syringe (cylindrical hollow piston with exterior mounted fluid tight seal) to move a fluid sample, and more particularly the capture of particulate matter on various membranes. While this prior art typically seeks to provide for a monolayer deposition it does not discuss a means to assess or adjust the amount of material captured on a filter device. Limitations are also discussed regarding the capture of multiple independent samples from a sample suspension. It is a further object of the present invention to allow multiple samples to be captured from the same or different sample suspensions, simultaneously.

United States co-pending application to Ferguson filed on Aug. 8, 2002, application Ser. No. 10/228,353, entitled "Method of depositing material and density gradients of material from sample suspensions and filter devices for same", discusses methods to capture and deposit a density gradient of material allowing the user to select a region having a desired amount of material for the intended purpose, such as cancer detection.

Various centrifuge systems provide a means to deposit material on a receiving surface, in some cases as a monolayer. U.S. Pat. No. 4,250,830, to Leif, entitled, "Swinging Buckets", discusses a cytology configuration for depositing multiple dispersions on a receiving surface.

U.S. Pat. No. 5,480,484, to Kelly, entitled, "Cytology centrifuge apparatus", and U.S. Pat. No. 5,679,154, to Kelly, also entitled "Cytology centrifuge apparatus", discuss use of a centrifuge for concentrating and depositing material, such as cells from one or more samples. U.S. Pat. No. 6,162,401 to Callaghan entitled, "Cytofunnel arrangement" also discusses material concentration and deposition, employing a cyto-funnel to prepare slides for microscopic examination.

U.S. Pat. No. 4,395,493 to Zahniser entitled "Monolayer device using filter techniques", discusses the need to have proper cell concentration in liquid suspension and a means to obtain a quantity of liquid having a desired number of cells as measured for example, with an impedance cell counter. In addition, Zahniser discusses existing methods of spreading cells onto a slide, using filter tape as a receiving surface and the general goals of monolayer deposition.

U.S. Pat. No. 5,784,193, to Ferguson, entitled "Microscope slide with removable layer and method" discloses a means to provide a removable structure on a microscope slide in the form of a surface layer which serves to confine and control the amount of material deposited on a microscope slide. Such removable layers adhere statically or rely on self-adhesive properties of mated materials (e.g. vinyl or silicone on smooth glass) or use pressure sensitive adhesives or are formed with evaporation layers of PVC, polymers, rubber, gaskets or other materials.

U.S. Pat. No. 4,614,109 to Hofmann entitled "Method and device for testing the permeability of membrane filters" discusses a means to assess the concentration and pore size of membranes as indicated by the differential pressure. For material capture the principal of assessing sample conditions, such as differential pressure, across a filter, and providing for capturing a desired amount of material are further discussed in U.S. Pat. No. 6,010,909, to Lapidus, entitled "Method and apparatus for controlled instrumentation of particles with a filter device", which among other things discusses use of a membrane filter that "is aperaturized with a uniform distribution of pores of substantially uniform size to block cells and other particles above a threshold size determined by the size of pores and to freely pass smaller particles". U.S. Pat. No. 6,225,125 to Lapidus, entitled, "Method and apparatus for controlled instrumentation of particles with a filter device", further discusses means to capture material on a filter device and more particularly means to capture a desired amount of material for monolayer deposition, for example. Relative to the present invention, this prior art is relatively expensive and complex utilizing various electronic means to monitor and control sample flow.

U.S. Pat. No. 4,792,398, to Klein, entitled, "Manual vacuum filtration device" discusses a porous membrane filter element interposed between a specimen receiving chamber and a vacuum chamber to retain solid particulate on the filter element. Further this prior art discusses recent attempts to provide apparatus for liquid filtering which are relatively small and operate by manual manipulation to cause a pressure differential.

U.S. Pat. No. 3,591,003, to Cooper, entitled "Differential pressure-responsive signaling device and filter assembly having same" discusses removal of contaminants from fluids such as lubricating oil, coolants and fuel. As the filter becomes obstructed with contaminants, the pressure differential across the filter increases (as sensed by the occurrence of a predetermined pressure differential) indicating that the filter is clogged and should be serviced. The principles of monitoring and responding to flow conditions are exploited for various embodiments of the present invention.

In addition, co-pending United States patent to Ferguson filed on Oct. 2, 2002, entitled "Filter device to capture a desired amount of material and methods of use" discusses a filter device, employed in various embodiments of the present invention, that may be used to capture a desired amount of material. And co-pending United States application to Ferguson filed on approximately Sep. 18, 2002, entitled, "Syringe device with resistive ridges and methods of use", discusses a novel syringe device with resistive ridges that may be used to provide a pressure source for some embodiments of the present invention. Accordingly, the prior art cited in this application is included by reference herein.

Therefore it is an object of the present invention to provide an apparatus and method to capture material at approximately a desired concentration for monolayer deposition, analysis or other uses, in a relatively simple and cost effective manner. It is a further object of the present invention to provide an apparatus and method that may be used to prepare multiple samples, simultaneously. It is a further object of the present invention, to provide apparatus and methods in a manner that may be further automated.

SUMMARY

It would be beneficial to provide a simple filter apparatus to capture a desired amount of material on a filter, and to transfer that material to a receiving surface for subsequent analysis, that does not rely on relatively complex electronics and sensors. In addition, it would be advantageous to provide a filter capture method that can be automated to prepare a plurality of samples, simultaneously. Accordingly, as will be further described, the present invention provides a novel apparatus incorporating a pressure transducer and means to substantially halt or otherwise adjust sample flow, and to transfer said material to a receiving surface, providing a simple, reliable device to capture a desired amount of material without complex electronics. In addition, the present invention is easily automated to allow material from a plurality of samples to be captured on a membrane filter, simultaneously, and subsequently transferred to a receiving surface for analysis.

As previously discussed herein, a variety of pressure sensors are available with appropriate characteristics for exploitation within the present invention. For some applications material captured on a filter is intended for contract-transfer to a receiving surface, such as a microscope slide. Accordingly, for some applications when a relatively large filter is required, or the suspending fluids are viscous, for example, a filter support structure may be desirable.

The present invention provides a filter apparatus using means to measure or sense the flow rate of a gas or liquid through a filter. In some embodiments pressure is sensed, however, the flow rate of a fluid or gas could also be sensed. In some embodiments, the present invention terminates or otherwise adjusts sample flow when a predetermined amount of material has been captured on a filter for example by venting the pressure differential responsible for sample flow, or closing the flow pathway, for example with a valve. In other embodiments of the present invention material collection on a filter is substantially reduced by restricting access to the filter, for example, by changing its position or deforming its shape.

Filter types include fibrous and mesh membranes, porous and capillary porous membranes, and fabric and gel lattices, for example. Such filters are commonly made from paper, nylon, glass fibers, nitrocellulose, polypropylene, chemical gels etc. In some cases filters are further treated to enhance certain properties such as capture capacity, flexibility, selectivity or adherence by coating them or incorporating other compounds such as PTFE or protein binding compounds. Accordingly, filters can be formed in various shapes such as planar, conical, pyramidal, hemispherical, spherical or filters may have their shape imposed by a carrier or other support structure.

BRIEF DESCRIPTION OF THE DRAWINGS

The organization and manner of the structure and operation of the preferred embodiments of the invention, together with further objects and advantages thereof, may best be understood by reference to the following description, taken in connection with the accompanying drawings, wherein like reference numerals identify like elements in which:

FIG. 1a (Prior art) Method to collect and monitor the concentration of material captured on a membrane filter FIG. 1b (Prior art) Membrane filter device used in conjunction with FIG. 1a.

DETAILED DESCRIPTION OF THE DRAWINGS AND PREFERRED EMBODIMENTS

Figure 1A:
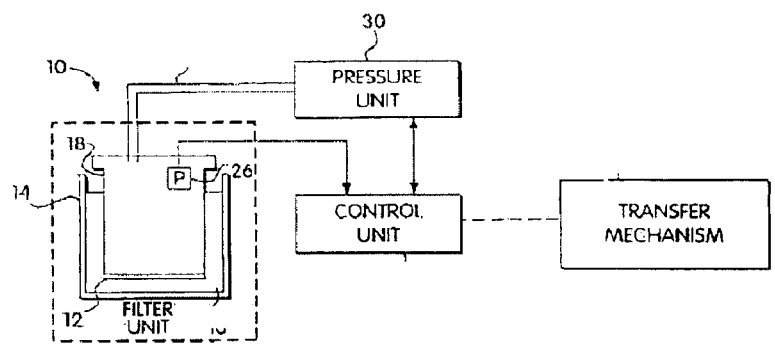

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Figure 1B:
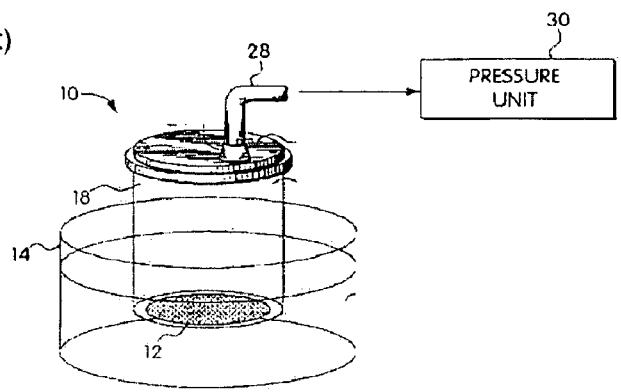

FIG. 1a (Prior art) illustrates a system 10 to collect a desired quantity of cells onto the underside of a screen-type filter 12. As diagrammed, a pressure sensor 26 is in communication with both sides of a membrane filter 12. Accordingly, one side of the membrane 12 in the collection vessel 18 is shown at ambient pressure with pressure sensor 26 provided on the opposite side of the membrane. Pressure unit 30 typically responds to electrical control signals from a control unit, which can be microprocessor controlled, to apply selected fluid conditions to the interior of the collection vessel. FIG. 1b (Prior art) further illustrates the collection vessel 18 with screen-type filter 12 as used in this apparatus, and as described in U.S. Pat. No. 6,010,909 and again in U.S. Pat. No. 6,225,125. In this manner, a desired quantity of material may be captured.

It would be beneficial to provide a simple filter capture apparatus that does not rely on relatively complex electronics and sensors. In addition, it would be advantageous to provide a system that can easily be automated to prepare a plurality of samples, simultaneously.

A variety of pressure sensors are available with appropriate characteristics for exploitation within the present invention. U.S. Pat. No. 6,295,877 to Aboul-Hosn, entitled "Pressure sensing cannula" discusses detecting the pressure of body fluids and further discusses a variety of pressure sensors and differential pressure sensors. U.S. Pat. No. 6,425,883 to Urich entitled "Method and apparatus for controlling vacuum as a function of ultrasonic power in an ophthalmic phaco aspirator" discusses methods to control vacuum and implement check valves to control aspiration. U.S. Pat. No. 4,996,627, to Zias, entitled, "High sensitivity miniature pressure transducer" further discusses pressure transducers and fabrication methods. U.S. Pat. No. 4,967,791 to Sternberger entitled "Pressure activated check valve" discusses means to measure and/or respond to pressure changes. U.S. Pat. No. 5,168,965 to Haung entitled "Bypass valve with selective characteristics for controlled and adjustable dashpots" also discusses a bypass valve with selective characteristics that incorporate pressure-activated check valves. As discussed above, Ferguson in copending US patent application discusses various filter devices to capture a desired amount of material. This prior art is included by reference herein.

Figure 2A:
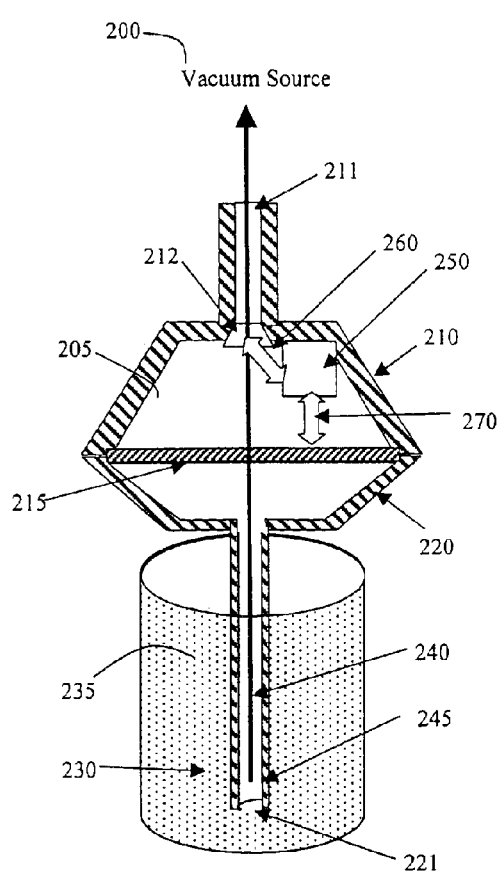
FIG. 2a shows a basic apparatus of the present invention to capture a desired amount of material for monolayer deposition.

FIG. 2a shows an embodiment of the present invention with filter apparatus 205 comprised of filter 215 deposed between a top body member 210 and a bottom body member 220. In this instance, open container 235 contains sample suspension 230 (e.g. particulate material suspended in a liquid) which is introduced via pickup tube 245. This pickup tube, as required or desired, may comprise part of the bottom body member 220 or pickup tube 245 may be a separate member attached to body member 220. The object of the device, which will now be further described, is to provide a means to monitor or otherwise sense the flow rate of this sample suspension 230 and to provide a means to alter, adjust, halt or otherwise influence that flow rate when indicated by sensor 250, which is in communication (mechanically or electro-mechanically) with the means to control flow. Sample suspension 230 is drawn by application of pressure from vacuum source 200 therefore providing a means to cause sample suspension 230 to flow as further indicated by flow directional arrow 240, which as diagrammed, is in the inlet port 221 of the pickup tube 245, into the bottom body member 220, through the filter 215, which is this instance is a membrane filter, through a flow control element 212 (in this instance a valve) and then out through the outlet port 211. Accordingly, as sample suspension 230 flows in this manner, particulate material in sample suspension 230 begins to be captured by membrane filter 215. Pressure sensor or pressure transducer 250, in this instance contained substantially within the top body member 210, communicates with the upper surface of membrane filter 215. This communication is further indicated by communication arrow 270. Pressure sensor 250 is also in communication with flow control element 212 so as to provide a means to adjust or otherwise control flow when certain pressures are sensed. This communication between pressure sensor 250 and flow control element 212 is further indicated by communication arrow 260. Accordingly, a pressure differential is established across the membrane filter 215, thereby providing a means for the pressure sensor 250 to monitor the flow rate of the sample suspension. As sample continues to flow, and as described in association with the description of prior art in FIGS. 1a and 1b, particulate material that is smaller than the pore size of the membrane filter 215 passes through the membrane (to waste or to another vessel—not shown) while material larger than the pore size of the membrane filter 215 is captured. Since filter pores provide the actual pathway through a filter, material captured by the filter typically blocks pores which in turn restricts flow. When the flow rate drops to a certain level, pressure sensor 250 responds, (at a predetermined pressure based on the application, filter characteristics, amount of desired material etc. as previously described herein and in the prior art cited) the pressure sensor 250 activates and in turn activates flow control element 212. The flow control element 212 may halt the flow of sample suspension and hence stop further capture of material on the membrane filter 215, the filter now having captured the desired amount of material. While such a valve (flow control element) could be implemented in various positions of within the filter assembly 205, generally communication with pressure sensor 250 is simpler and provides more options when these two functions are relatively closely related. Further examples of this will be provided in the descriptions accompanying FIGS. 2b and 2c. Activation of the flow control element 212 may be mechanical, electromechanical or may be accomplished via further integration of the pressure sensor and valve (as will be further discussed). Similarly, these elements may be physically separate or may be functionally integrated. For applications, such as monolayer deposition, that may require access to the filter for touch or other material transfer method, the top body member 210 and bottom body member of filter apparatus 205 are preferably made separable, by employing threads or a press-fit assembly, for example.

Figure 2B:
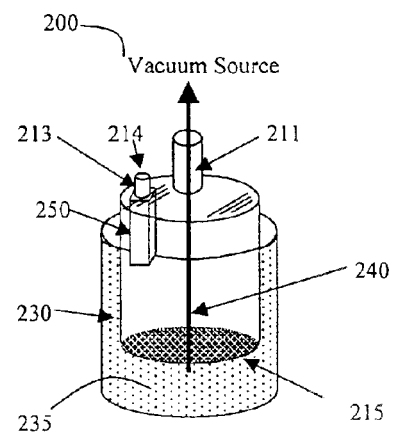
FIG. 2b shows another embodiment of the present invention

FIG. 2b shows another embodiment of the present invention with sample suspension 230 being drawn through filter 215 by application of vacuum 200. In this instance filter 215 is sealed to the bottom of upper body member 210 thereby providing access to material captured by membrane filter 215. As diagrammed the sensor 250 is integrated with flow control element 213, which in this instance provides flow control using a valve to vent the pressure source 200 through vent port 214 or flow control valve 213, rather than adjusting the sample flow pathway, as described in association with FIG. 2a. As required, or desired, the vent may substantially release the vacuum supplied by source 200 to halt flow, or the drop in vacuum provided by this venting may be sensed and the vacuum source, shut off.

Figure 2C:
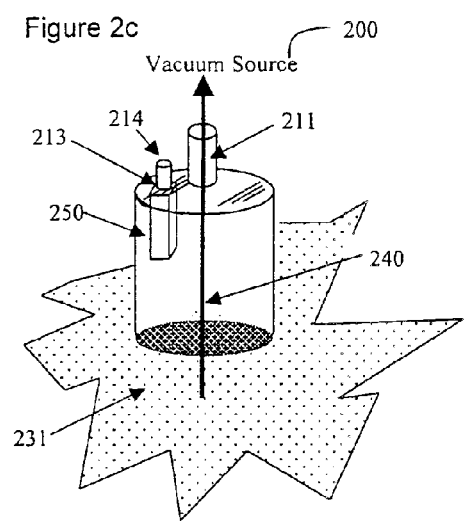
FIG. 2c shows yet another embodiment of the present invention used to capture a desired amount of particulate material suspended in a gas.

FIG. 2c shows application of the device and configuration of the present invention described in association with FIG. 2b where sample suspension 231 consists of particulate matter, for example, soot, suspended in a gas, for example air.

Figure 3A:
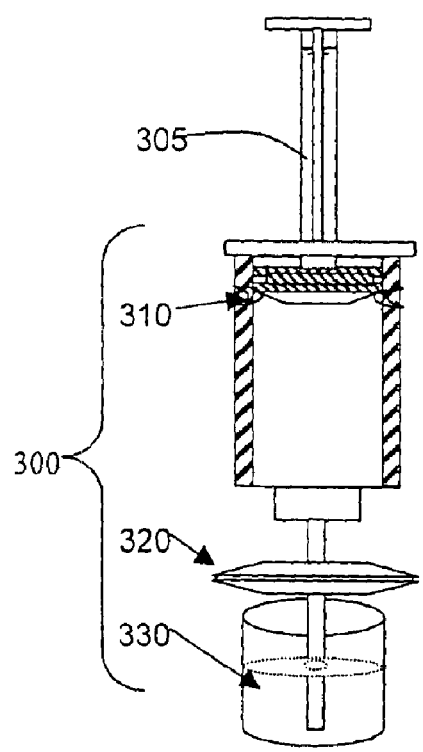
FIG. 3a shows the embodiment of FIG. 2a where a novel syringe device serves as a vacuum source.

FIG. 3a shows use a filter apparatus 300 of the present invention comprising a novel filter device 320 positioned to capture a desired amount of material from sample suspension 330. A novel syringe 305 further provides a means to supply pressure to aspirate some of the sample suspension 330 through the filter device.

The unique functionality of this syringe is provided by a resistive ridge in the form of stop 310 formed in the barrel of the syringe to restrict movement of the syringe plunger and attached gasket, thereby supplying a vacuum to aspirate sample when the syringe gasket is retracted past this tactile stop.

Figure 3B:
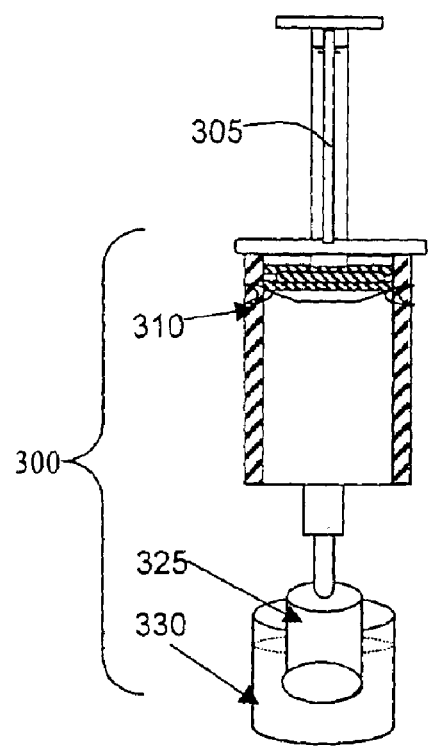
FIG. 3b shows the embodiment of FIG. 2b where a novel syringe device serves as a vacuum source.

FIG. 3b shows use a filter apparatus 300 of the present invention comprising a novel filter device 325 having an exposed membrane filter on the lower surface so as to capture a desired amount of material from sample suspension 330. A novel syringe 305, as further describe in association with FIG. 3a provides pressure to draw sample suspension 330 through the filter device for material capture.

The syringe device may be selected with dimensions and characteristics so as to provide sufficient vacuum to aspirate more fluid suspension than would be required to prepare an adequate sample from relatively a dilute sample. For some applications it may be advantageous to develop sufficient vacuum so that this pressure remains relatively constant over some desired operating range. Alternative means of providing vacuum for monolayer material capture and deposition are further described herein for various embodiments of the present invention. As required or desired, the features of pressure sensing and flow control as described in association with FIGS. 2a, 2b an 2c could be further integrated with the filter into the syringe barrel to form a single functional unit.

Figure 4:
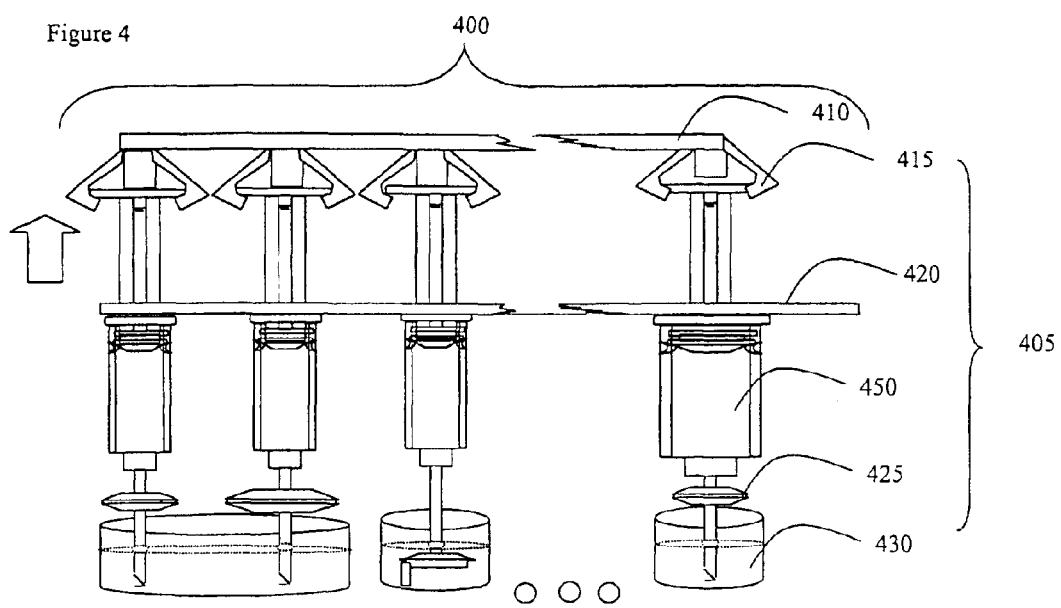
FIG. 4 shows the present invention configured for automation to capture a plurality of samples for use, such as monolayer deposition

FIG. 4 shows a plurality of filter apparatus 400 configured as sample stations 405, connected by structural member 420. Although each syringe device 450 could be driven individually by a stepper motor or other means, the unique filter devices 425, as further described in association with FIGS. 2a, 2b and 2c comprise a means to sense pressure and further control flow so as to provide independent means for each sample station 405 to capture a desired amount of material from a sample suspension 430.

The retractor(s) may be moved in a controlled manner to provide additional control over sample aspiration. The dimensions of the syringe, the particulate material being captured, viscosity of the fluid, the filter characteristics and filter area and other factors are considered when selecting components for a particular application. Similarly, the pressure transducer(s) used in the filter devices may be designed to trigger at a single predetermined pressure or their response characteristics may be made adjustable using potentiometric, tension or other means. For some applications, such as the examination of cytological samples by machine vision, the receiving surface for monolayer deposition may comprise a cover-glass or other relatively thin, uniform material, such as transparent tape, thereby providing material at approximately the same distance from the top surface to facilitate focus.

Figure 5:
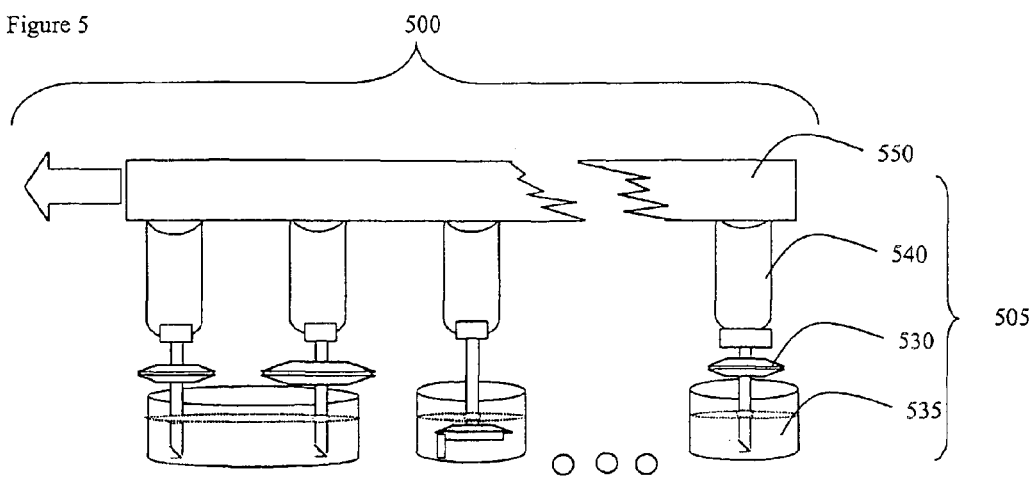
FIG. 5 shows another configuration automating the present invention to capture a plurality of samples, simultaneously.

FIG. 5 shows a plurality of filter apparatus 500 of the present invention arranged as sample stations 505, each configured to capture a desired amount from their respective samples. As diagrammed, vacuum manifold 550 distributes vacuum which may be further held relatively constant by various means, such as vacuum isolator tanks 540. Again as described herein, as material from sample suspensions 535 are drawn through their respective filter devices 530, some material is captured and begins to occlude the filter causing pressure changes across the filter, which are sensed. At a predetermined pressure, indicating that a desired amount of material has been captured, the sensor activates or otherwise interacts with a means to control flow halting further material capture for that particular sample station.

While preferred embodiments of the present invention are shown and described, it is envisioned that those skilled in the art may devise various modifications of the present invention without departing from the spirit and scope of the appended claims.

I claim:

1. An apparatus for capturing a desired quantity of material from a sample suspension, comprising:

a body member having an inlet port and an outlet port forming a single pathway through said apparatus for flow of sample suspension;

a filter housed in said body member in said pathway;

means for creating a flow of sample suspension through said filter by negative pressure;

a sensor to measure a pressure differential across said filter;

a flow control element in said body member downstream of said filter and in mechanical communication with said sensor, whereby said sensor activates said flow control element to vent said single pathway when a desired amount of material has been captured by said filter, to stop said flow of said sample suspension through said apparatus; and means for removing said captured material for subsequent analysis.

2. The apparatus of claim 1, wherein said sensor and said flow control element are integrated.

3. The apparatus of claim 2, wherein said sensor and said flow control element comprise at least one poppet valve.

4. The apparatus of claim 3, wherein said at least one poppet valve is adjustable.

5. The apparatus of claim 2, wherein said sensor and said flow control element comprise at least one pressure-sensitive check valve.

6. The apparatus of claim 5, wherein said at least one pressure-sensitive check valve is adjustable.

7. The apparatus of claim 1, further comprising a surface for receiving material captured on said filter.

* * * * *